United States Patent [19]
Regula et al.

[11] Patent Number: 5,674,921
[45] Date of Patent: Oct. 7, 1997

[54] RADIATION-CURABLE, URETHANE-ACRYLATE PREPOLYMERS AND CROSSLINKED POLYMERS

[75] Inventors: Donald W. Regula, Belle Meade; Michael F. Bregen, Lebanon, both of N.J.; Stuart L. Cooper, Wilmington, Del.; Dennis D. Jamiolkowski, Long Valley; Rao S. Bezwada, Whitehouse Station, both of N.J.

[73] Assignee: Ethicon, Inc., Somerville, N.J.

[21] Appl. No.: 382,325

[22] Filed: Feb. 1, 1995

Related U.S. Application Data

[62] Division of Ser. No. 916,326, Jul. 17, 1992.
[51] Int. Cl.$^6$ .............. A61B 17/08; G03C 5/00; B29C 35/02; C08L 75/16
[52] U.S. Cl. .................. 522/97; 522/96; 528/80; 528/81; 528/84; 525/455; 525/453; 264/22; 430/269; 606/157; 606/158; 606/154
[58] Field of Search ............. 522/97, 96; 528/80, 528/81, 84, 85; 525/453, 455, 462; 430/269; 264/22; 606/154, 157, 158

[56] References Cited

U.S. PATENT DOCUMENTS

| Re. 29,131 | 2/1977 | Smith et al. ............... 260/77.5 |
|---|---|---|
| 4,153,776 | 5/1979 | Friedlander et al. .......... 522/96 |
| 4,284,506 | 8/1981 | Tetenbaum et al. ........... 210/321.4 |
| 4,804,691 | 2/1989 | English et al. .............. 523/118 |
| 5,034,461 | 7/1991 | Lai et al. .................. 525/100 |
| 5,145,945 | 9/1992 | Tang et al. ................. 528/370 |
| 5,173,301 | 12/1992 | Itah et al. ................. 528/70 |
| 5,490,962 | 2/1996 | Cima et al. ................. 264/255 |
| 5,521,280 | 5/1996 | Reilly et al. ............... 528/370 |

FOREIGN PATENT DOCUMENTS

| 290 623 | 11/1988 | European Pat. Off. . |
|---|---|---|
| WO 89/08021 | 9/1989 | WIPO . |

OTHER PUBLICATIONS

Koshiba et al, "Properties of Ultra-Violet Curable Polyurethane Acrylates", *Journal of Materials Science* 17, (1982), pp. 1447–1458.
Derwent Publication AN 86–262018 Abstract of JP-A-61 190 519.
Lai et al., J. Appl. Polym. Sci., 42, 2039 (1991).
Lai et al., J. Appl. Polym. Sci., 42, 2833 (1991).
Lai et al., Polymer Preprints, 31, 689 (1990).
Lai et al., Polymer Preprints, 31, 687 (1990).
Lai et al., Polymer Preprints, 31, 584 (1990).
Oraby et al., J. Appl. Polym. Sci., 23 3227 (1979).
Oraby et al., J. Appl. Polym. Sci., 23, 3243 (1979).
Koshiba et al., J. Mater. Sci., 17, 1447 (1982).
Speckhard et al., J. Appl. Polym. Sci, vol. 30 647–666 (1985).
Nagarajan et al., Polym. Eng. and Sci., 26, 1442 (1986).
Nakazoto et al., J. Appl. Polym. Sci., 38, 627 (1989).
Lin et al., Chem. Eng. Commun., 30, 251 (1984).
Pennings, A.J., BIomaterials 1990, vol. 1, May.
Pennings, A.J., Makromol. Chem., Rapid Commun. 4, 675–680 (1983).
Pennings, A.J., Makromol. Chem., Rapid Commun. 9, 589–594 (1988).

*Primary Examiner*—Susan W. Berman
*Attorney, Agent, or Firm*—Hal Brent Woodrow

[57] ABSTRACT

A radiation-curable prepolymer of a polyurethane endtipped with an hydroxy (acrylate or methacrylate) is disclosed. The polyurethane is derived from the reaction of a polyfunctional isocyanate with a hydrolyzable oligomer of an anhydrous cyclic ester of an hydroxy acid. Crosslinked polymers prepared by irradiating the prepolymers are also disclosed. The crosslinked polymers are bioabsorbable and biocompatible with bodily tissue, yet still maintain the outstanding mechanical properties one would expect from a polyurethane. The prepolymers and crosslinked polymers are especially well-suited for the fabrication of surgical devices, particularly wound closure devices such as surgical staples and clips, in a stereolithography apparatus.

20 Claims, 4 Drawing Sheets

RADIATION-CURABLE, URETHANE-ACRYLATE PREPOLYMERS AND CROSSLINKED POLYMERS

This is a division, of application Ser. No. 07/916,326, filed Jul. 17, 1992, which is hereby incorporated by reference.

BACKGROUND OF THE INVENTION

This invention relates to urethane prepolymers, especially polyester-based urethane prepolymers, and crosslinked polymers prepared from these prepolymers. More specifically, it relates to urethane-acrylate prepolymers which can be cured by irradiation to form bioabsorbable polyurethanes, and therefore are especially well suited for use in preparing biomedical devices in a stereolithography apparatus (SLA).

The ability to custom design biomedical devices rapidly and efficiently, and to make modifications to the design of existing devices on short notice, is critical to the success of any business specializing in the production of such devices. Conventionally, biomedical devices are molded in an injection molding apparatus. However, before the device can be shaped to required design specifications in the mold, the mold itself must be designed to meet those specifications, and then subsequently fabricated. This requires significant time and resources, and so consequently, alternatives to conventional molding techniques have been sought.

One possible alternative to conventional molding techniques is stereolithography (SL). SL is a new technology which may provide a significant opportunity to create biomedical devices with specifically tailored properties more quickly, more accurately, and more economically than devices created using conventional molding techniques. SL would bypass the need to design a mold to fit the criteria required for the device, as well as the fabrication of the mold itself. Devices could be manufactured directly from a Computer Aided Design (CAD) model that could drive the SLA.

One of the requirements necessary to utilize SL technology is the preparation of monomer or prepolymer compositions which can be cured by conventional irradiation techniques involving exposure to UV light in the presence of a photoinitiator. While numerous monomer and prepolymer compositions can be cured thermally to prepare biomedical devices, certain monomer and prepolymer compositions must be especially adapted so they are suitable for curing using irradiation techniques.

Polyurethanes have been extensively studied for a wide array of uses, including uses for biomedical applications. More significantly, urethanes functionalized with an acrylate functionality have also been prepared and extensively studied as radiation-curable prepolymers. For example, Lai et al., J. Appl. Polym. Sci., 42, 2039 (1991), discloses preparing a radiation-curable, urethane-acrylate prepolymer formed from the reaction of a polyol oligomer with a diisocyanate, which reaction product is subsequently end-capped with hydroxyethyl methacrylate (HEMA). The cured materials are claimed to have potential for biomedical device applications. In a related article, Lai et al., J. Appl. Polym. Sci., 42, 2833 (1991), discusses the hydrolytic stability of polyurethane hydrogels made by curing the previously disclosed prepolymers, and then saturating the cured material with buffered saline. The stability is reported to be significantly affected by curing conditions, and the polyurethane hydrogels are disclosed as having applications for use as contact lenses and surgical implants. The following companion articles further research the hydrolytic stability and other properties of polyurethane hydrogels especially suited for ophthalmic applications: a) Lai et al., Polymer Preprints, 31, 689 (1990); b) Lai et al., Polymer Preprints, 31, 687 (1990); and c) Lai et al., Polymer Preprints, 31, 584 (1990). Also authored by Lai is U.S. Pat. No. 5,034,461, which discloses novel urethane prepolymers useful in biomedical applications.

Furthermore, the polyol oligomer chosen to prepare urethane-acrylate prepolymers, and its molecular weight, has been extensively studied to determine its effect on the mechanical properties of the cured polyurethane. Oligomers investigated include polycarbonates, polypropylene oxide, polytetramethylene oxide, polydimethyl siloxane, ethylene glycol/adipic acid, polytetramethylene adipate, polybutadiene, and, most significantly, polycaprolactone, which is known to be biocompatible with bodily tissue, and therefore especially well suited for biomedical applications. For a detailed review of polyurethanes made from these oligomers, see the following articles: Oraby et al., J. Appl. Polym. Sci., 23, 3227 (1979); Oraby et al., J. Appl. Polym. Sci., 23, 3243 (1979); Koshiba et al., J. Mater. Sci., 7, 1447 (1982); Speckhard et al., J. Appl. Polym. Sci., 30, 647, (1985); Nagarajan et al., Polym. Eng. and Sci., 26, 1442 (1986); Nakazoto et al., J. Appl. Polym. Sci., 38, 627 (1989); Lin et al., Chem. Eng. Commun., 30, 251 (1984). Although the radiation-curable, urethane-acrylate prepolymers disclosed in the literature can be tailored to produce cured polyurethanes with a wide array of physical and mechanical properties especially adapted for biomedical applications, these polyurethanes have one major drawback. For numerous applications, especially for those applications requiring a surgical device which is to be implanted in bodily tissue, the polymer from which the device is prepared must be bioabsorbable. In other words, the device must be capable of breaking down into small, non-toxic segments which can be metabolized or eliminated from the body without harm.

Unfortunately, although the urethane-acrylate prepolymers described above can be cured with UV light to prepare polyurethanes, which can subsequently be used in the form of a hydrogel for certain biomedical applications, such hydrogels are not absorbable in bodily tissue. Since these polyurethane hydrogels are nonabsorbable in bodily tissue, surgical implants made from these polyurethane hydrogels would remain indefinitely within the bodily tissue, possibly causing adverse tissue reaction or other complications associated with the confinement of foreign matter in bodily tissue.

It is worthy to note at this point that biodegradable polyurethanes have been made for medical applications. See, for example, the work A. J. Pennings has described for preparing a wound covering from biodegradable poly(ester-urethane) elastomer networks, in the following references: Biomaterials 1990, Vol. 1, May; Makromol. Chem., Rapid Commun. 4, 675–680 (1983); and Makromol. Chem., Rapid Commun. 9, 589–594 (1988). Unfortunately, the compositions from which the wound coverings are derived are not radiation-curable, and therefore would not be amenable for use in preparing biomedical devices in an SLA.

In view of the deficiencies in the prior art for preparing radiation-curable, urethane prepolymers especially adapted for numerous biomedical applications requiring the use of an implantable bioabsorbable device, what is needed is a urethane prepolymer which can be cured to form a bioabsorbable polyurethane. In addition, it would be highly desirable if such a prepolymer could be produced which is capable of being cured by conventional irradiation techniques to prepare a crosslinked polymer with outstanding mechanical properties, and therefore would be amenable for use in an SLA.

SUMMARY OF THE INVENTION

In one aspect, the invention is a radiation-curable, urethane-acrylate prepolymer. This prepolymer comprises the reaction product of the following components:

a) a urethane prepolymer of a polyfunctional isocyanate and a hydrolyzable oligomer of an anhydrous cyclic ester of an hydroxy acid, and b) an endtipping amount of an hydroxy (acrylate or methacrylate).

In another aspect, the invention is a crosslinked polymer prepared by irradiating the urethane-acrylate prepolymer defined above. The conditions of irradiation must be sufficient to induce curing of the prepolymer.

The urethane-acrylate prepolymers of this invention can be made from numerous readily-available raw materials. The prepolymers can be cured to form crosslinked polymers using conventional irradiation techniques such as photopolymerization in the presence of ultraviolet (UV) light. The crosslinked polymers exhibit outstanding mechanical properties, for example, those properties relating to tensile strength, elongation and modulus.

Surprisingly, the crosslinked polymers in preferred embodiments of this invention are bioabsorbable and biocompatible with bodily tissue. These desirable properties are derived from the incorporation of the hydrolyzable oligomer into the backbone of the crosslinked polymer. Furthermore, these properties can be obtained without appreciably sacrificing the mechanical properties of the crosslinked polymer.

The properties of the urethane-acrylate prepolymers and crosslinked polymers within the scope of this invention are particularly well matched for the preparation of bioabsorbable, implantable medical and surgical devices using SL. Such implantable devices include, but are not limited to, wound closure devices such as surgical clips and staples.

Certain embodiments of our urethane-acrylate prepolymers can be applied directly to bodily tissue and irradiated in situ to form barriers, and/or act as tissue adhesives. In some cases, adhesion-prevention barriers can be formed in situ.

DETAILED DESCRIPTION OF THE INVENTION

Figure 1:
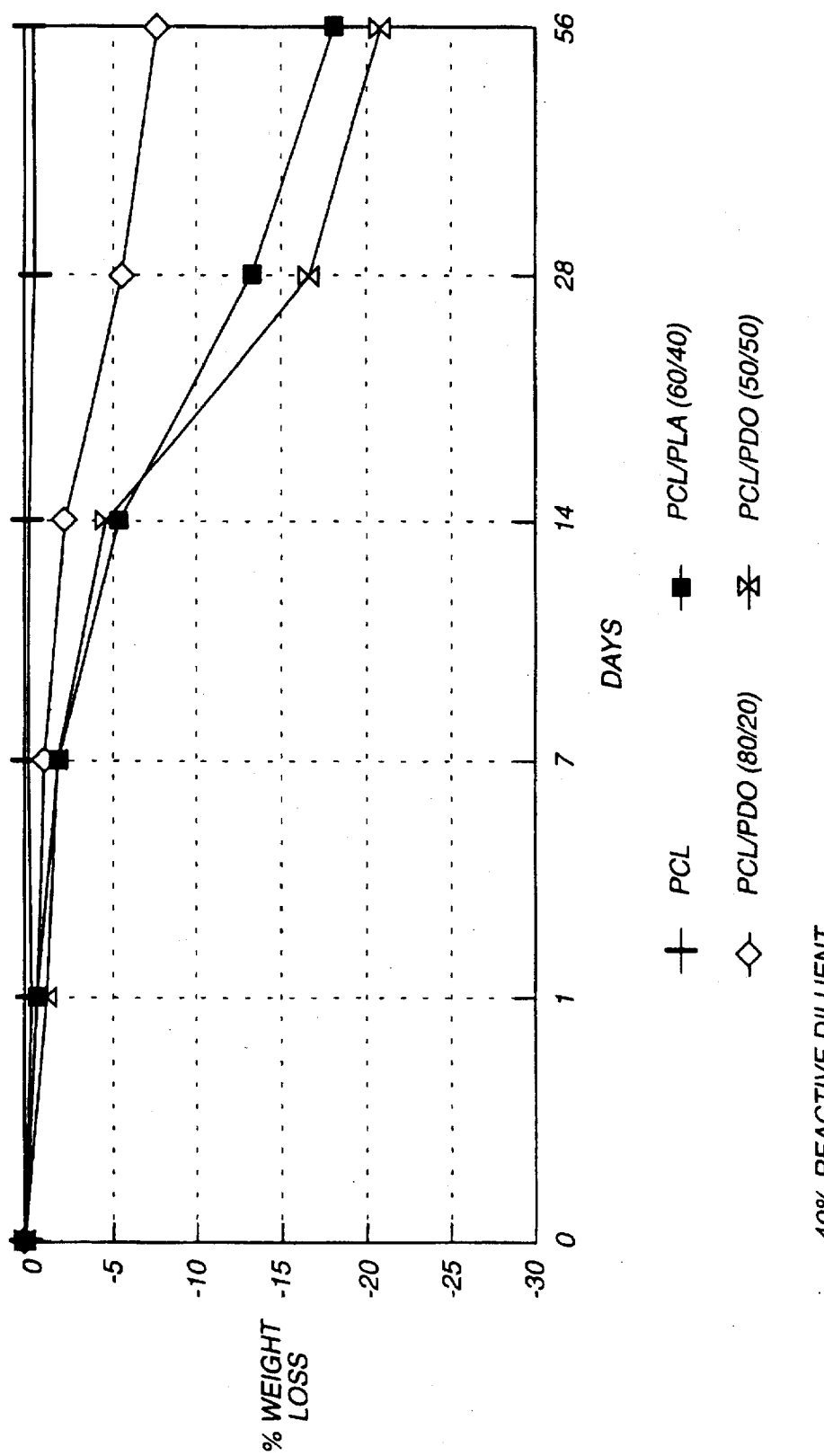
FIGS. 1–4 show a plot of the in vitro weight loss in a buffered saline solution of various crosslinked polymers of this invention over time. A plot of the weight loss for a crosslinked polymer which did not incorporate a hydrolyzable oligomer is shown for comparison.
Figure 2:
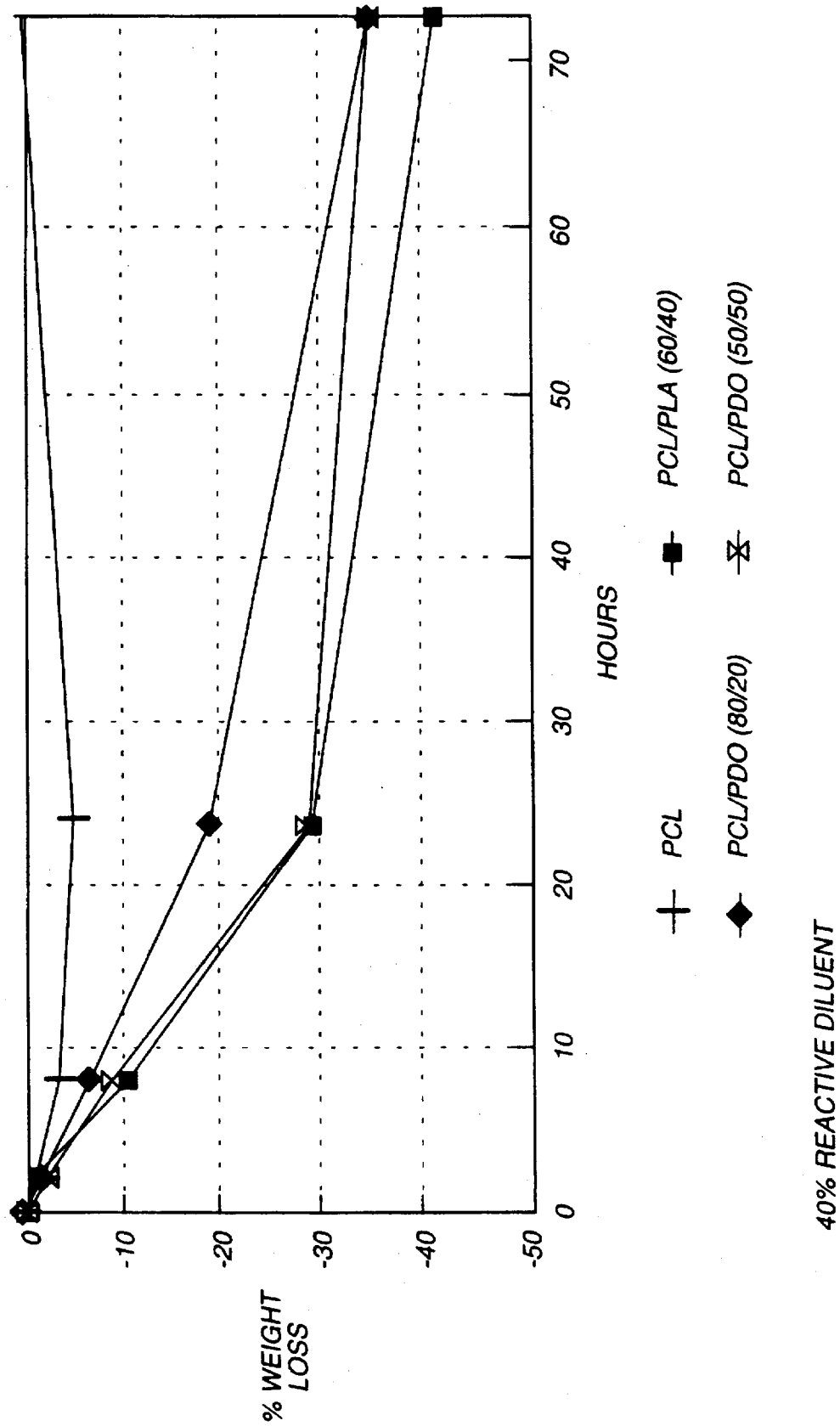
Figure 3:
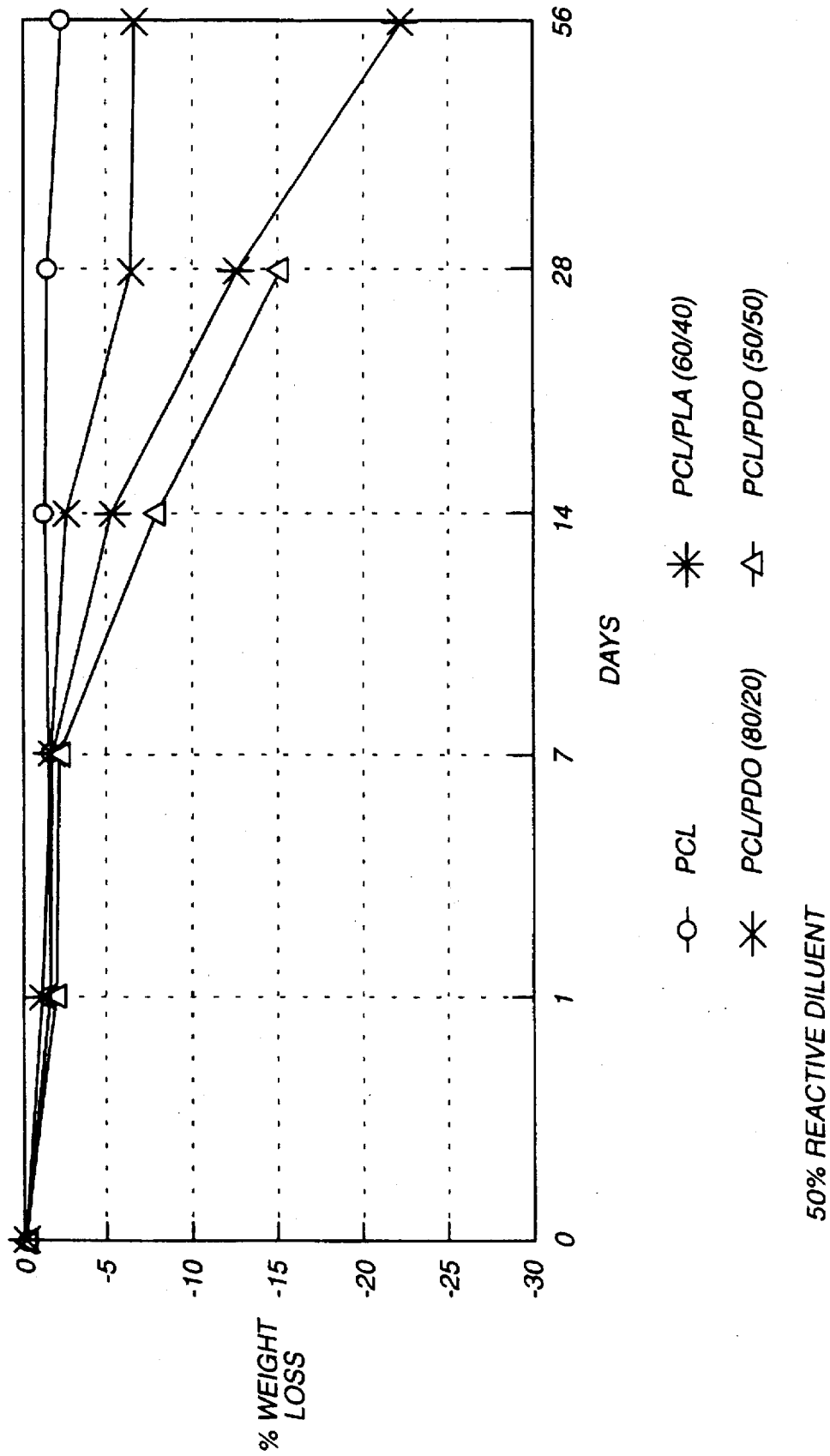
Figure 4:
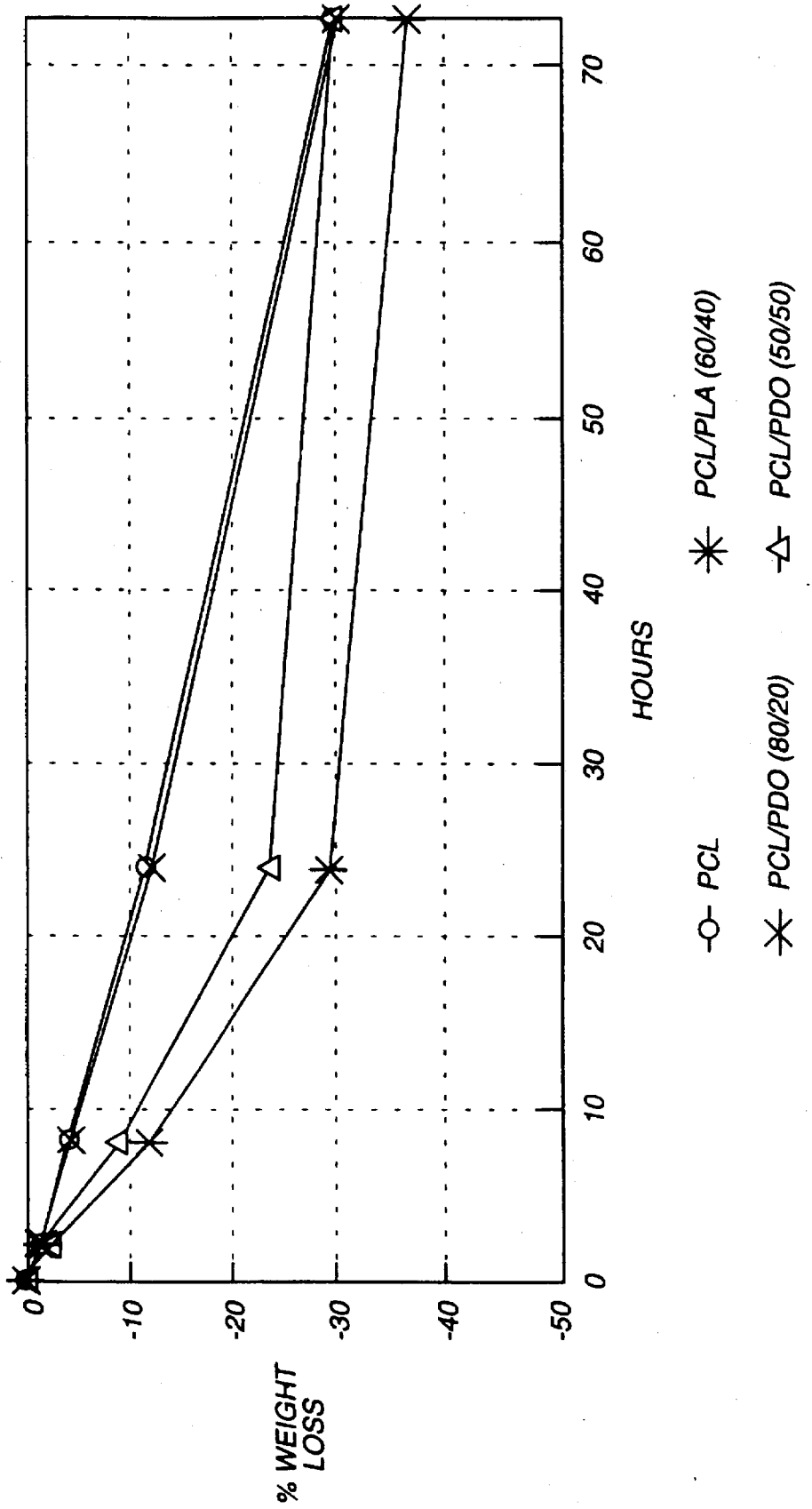

Anhydrous cyclic esters of hydroxy acids are well known compounds, many of which, when polymerized, form biocompatible and bioabsorbable polymers commonly used for biomedical applications. These esters are commonly referred to as lactone monomers, and include lactide, glycolide, para-dioxanone, and trimethylene carbonate. Strictly speaking, some may not consider trimethylene carbonate an anhydrous cyclic ester of a hydroxy acid, but for purposes of this invention, it may be considered to function as such. Comonomer mixtures of these lactone monomers with ε-caprolactone are frequently used for biomedical applications. A preferred mixture is ε-caprolactone and either para-dioxanone or lactide. When this mixture is used, the preferred mole ratio of caprolactone to either para-dioxanone or lactide is between about 10:90 to about 90:10, more preferably between about 20:80 to about 80:20, and most preferably between about 60:40 to about 40:60.

The hydrolyzable oligomer can be prepared using standard polymerization techniques for the polymerization of lactone monomers. See, for example, the synthesis procedures subtitled "Synthesis of Hydrolyzable Oligomers of Anhydrous Cyclic Esters of Hydroxy Acid", described in the Examples. The weight average molecular weight of the oligomer, as measured by gel permeation chromatography, is desirably between about 500 to about 5000. A preferred oligomer is between about 2000 to about 3000. If the molecular weight is below about 500, then there is a possibility that the crosslinked polymer derived from the urethane-acrylate prepolymer of this invention would be too brittle for numerous applications. If the oligomer molecular weight were greater than about 5000, then its viscosity may be too high for convenient processing, which could affect the properties of the crosslinked polymer.

For purposes of defining this invention, the oligomer is "hydrolyzable" if it reacts with water or a buffered aqueous solution and experiences a significant weight loss. Complete hydrolysis may take several months, although preferably hydrolysis will be complete within 12 months and most preferably within 6 months. It is to be understood that some enzymatic degradation can take place and still be within the scope of this invention. The lactone monomers and comonomer mixtures described above lead to polymers which are known to be hydrolyzable, unlike commonly used polyol oligomers for the preparation of polyurethanes.

Polyfunctional isocyanates which can be used to prepare the urethane prepolymer are the diisocyanates, triisocyanates, and polyfunctional monoisocyanates, including those isocyanates which can be derived from biologically active amino acids, for example, lysine diisocyanate or lysine triisocyanate. For a description of typical diissocyanates which can be used to prepare polyurethanes, see, for example, "Polyurethanes in Medicine", Cooper, S. L. and M. D. Lelah, CRC Press (1986); "Polyurethanes: Chemistry and Technology" Parts I & II, Saunders, J. H. and K. C. Frisch, Interscience, New York, (1962); and "Polyurethane Handbook", B. Oertel, Hauser Publishers, New York (1985).

The preferred diisocyanates are toluene diisocyanate, isophorone diisocyanate, (meta) tetramethyl xylene diisocyanate, and 4,4'methylene diphenylene diisocyanate. The preferred triisocyanate is lysine triisocyanate, and the preferred polyfunctional monoisocyanate is isocyanatoethyl methacrylate. The preferred class of polyfunctional isocyanates are the diisocyanates because of the optimum degree of crosslinking which diisocyanates provide for the preparation of ductile crosslinked polymers. The most preferred diisocyanates are toluene diisocyanate (TDI) and isophorone diisocyanate (IPDI).

The urethane prepolymer can be prepared by reacting the polyfunctional isocyanate with the hydrolyzable oligomer at slightly elevated temperatures exceeding room temperature. The mole ratio of oligomer to isocyanate should be an amount to provide for essentially complete reaction, which amount is advantageously an amount defined by a mole ratio of oligomer to isocyanate of about 2:1. The reaction mixture is desirably stirred, and the reaction is usually exothermic. The incorporation of an organometallic catalyst at a concentration of about 0.1 weight percent of the reaction mixture, may be desired depending on the reaction components used.

The preferred hydroxy acrylate or hydroxy methacrylate to endtip the urethane prepolymer is either hydroxyethyl methacrylate (HEMA) or hydroxyethyl acrylate (HEA). However, other hydroxy acrylates or methacrylates can be used, for example, difunctional acrylates such as ethylene glycol dimethacrylate can be used if a greater degree of crosslinking is desired. The most preferred hydroxy acrylate or hydroxy methacrylate is an hydroxy methacrylate, most preferably HEMA.

The amount of the hydroxy acrylate or hydroxy methacrylate required to endtip the urethane prepolymer is desirably an amount which will provide for essentially complete reaction of the acrylate. The mole ratio of the acrylate to the prepolymer can range from about 1:2 to about 2:1, but desirably it is about 1:1. The endtipping reaction can be simply carried out by adding the required amount of the chosen acrylate to the prepolymer reaction mixture, and maintaining an elevated temperature exceeding room temperature for an appropriate period of time, e.g. three hours.

The urethane-acrylate prepolymer can be polymerized to form a crosslinked polymer by irradiation under appropriate conditions. These conditions may include polymerization by irradiation with gamma or x-rays, but preferably it involves photopolymerization by exposure to UV light in the presence of a photoinitiator. Numerous photoinitiators or photosensitizers can be used. A preferred class of photoinitiator is the acetophenone derivatives and, particularly 2,2-diethoxyacetophenone at a concentration of no greater than about 1 weight percent of the reaction mixture. The photoinitiator is added to the reaction mixture before curing, and then the reaction mixture is exposed to UV light. The optimum conditions for photopolymerizing the reaction mixture in the presence of UV light can readily be determined empirically.

To aid in the processing and curing of the urethaneacrylate prepolymer, it may be desirable or necessary in some instances to carry out the irradiation step at slightly elevated temperatures, e.g. 40°–50° C., to prevent crystallization of the prepolymer matrix.

In an especially preferred embodiment of this invention, irradiation of the prepolymer occurs in the presence of a reactive diluent. A reactive diluent may often be desirable or necessary because the reaction of the hydrolyzable oligomer with the isocyanate, and the subsequent reaction with the acrylate, can often significantly increase the molecular weight of the prepared urethane-acrylate prepolymer, which consequently increases its viscosity. Often, the prepolymer is a viscous fluid, with a viscosity less than about 100,000 centipoise (cps). Increased viscosity such as this may make it difficult to process and cure the prepolymer without the aid of a reactive diluent.

The reactive diluent is advantageously a compound which possesses ethylenic unsaturation. In addition, it desirably is capable of solubilizing the prepolymer to form a homogeneous solution, and has a relatively low volatility with a boiling point of no less than about 200° C. The preferred diluents include HEMA and N-vinyl pyrrolidinone.

The amount of reactive diluent added to the reaction mixture should be an amount such that the viscosity of the formed prepolymer solution is between about 500 to about 2000 cps. This viscosity range can be achieved by adding about 20 to about 70 weight percent diluent based on the weight of the total reaction mixture, preferably between about 40 to about 50 weight percent. Lower amounts of diluent may not be enough to achieve an optimum viscosity for processing, while a higher amount of diluent may adversely affect the curing or may cause an appreciable decrease in the mechanical properties of the crosslinked polymer.

If HEMA is used as not only the reactive diluent but also the endtipping acrylate, then excess HEMA could be added to endtip the urethane prepolymer, and the unreacted HEMA could function as the diluent without the need to separately add additional HEMA for this purpose.

After the prepolymer is cured by irradiation to form a crosslinked polymer, it may be desirable to post-cure the crosslinked polymer at elevated temperatures exceeding room temperature under vacuum for approximately for about 24 hours with or without the presence of a UV-source to remove or react any unreacted components and diluent.

The crosslinked polymers of this invention, in the preferred embodiments, are bioabsorbable and biocompatible with bodily tissue. The crosslinked polymers will completely bioabsorb in bodily tissue within about three years, preferably within about one year, and most preferably within about six months. The bioabsorbability of the crosslinked polymers is achieved without sacrificing mechanical properties. It is possible to achieve a range of mechanical properties depending on the choice of the oligomer type and molecular weight of the polyfunctional isocyanate and the type and concentration of reactive diluent. This is illustrated by the tensile results shown in Table 4 for the cured prepolymers. The ideal range of properties will depend on the intended use of a device. For example, for a ligating clip device, ductility is an important property. For this application, ideally an elongation greater than about 50 percent, preferably greater than about 100 percent is desired. The crosslinked polymers exhibit a preferred tensile strength greater than about 3000 psi, and a modulus greater than about 100,000 psi.

The urethane-acrylate prepolymers can be readily cured by irradiation in an SL apparatus, and therefore can be shaped to form numerous medical and surgical devices composed of crosslinked polymers with outstanding mechanical properties. For example, the prepolymers of this invention can be cured in an SLA apparatus to form wound closure devices such as surgical staples and clips, as well as any other surgical devices especially adapted for implantation in bodily tissue.

The following examples are provided to illustrate particular embodiments which fall within the scope of the claimed invention, but those skilled in the art can readily appreciate that numerous additional embodiments fall readily within the scope of the appended claims.

EXAMPLES

CONTROL EXAMPLES 1–8

Materials and Synthesis, Non-absorbable Urethane Acrylate Controls (for Comparison with the Absorbable, Urethane-Acrylates of the Inventions):

Polycaprolactone diol (PCL) was obtained from Aldrich Chemical Company. Polamine, benzylamine terminated polytetramethylene oxide (POL) was obtained from Air Products Corporation. PCL was dried for 24 hours at 70° C. under vacuum prior to use. IPDI was purchased from Aldrich Chemical. Lysine triisocyanate, LTI, was obtained from Tory Industrie. HEMA and NVP were purchased from Aldrich. Dibutyl tin dilaurate (DABCO T12) catalyst was purchased from Air Products. The initiator, 2,2 diethoxyacetophenone (DEAP), was purchased from Polysciences.

The synthesis procedure is outlined below:

i) Synthesis of the urethane
(The amounts listed are for a typical laboratory batch size. The amounts can be scaled accordingly).

Charge 25 grams of polyol (e.g., PCL-2000 or POL-2000 to glass jar. Heat to 60° C. Slowly add 5.6 gm of the diisocyanate e.g., IPDI. For PCL add 1–2 drops of T-12 catalyst. Mix at room temperature for 5 minutes by shaking the jar. Heat for 1 hour at 65° C.

ii) Synthesis of urethane acrylate

Add 3.25 9 of end tipping group e.g., HEMA. For POL add 1–2 drops of T-12 catalyst. Mix for 5 minutes. Heat for 3 hours at 65° C. Cool to room temperature slowly in air. Store at least overnight at room temperature in the dark. Materials could be stored longer without an adverse effect, but storage times should be kept to a minimum because without inhibitor, this material will eventually crosslink.

iii) Addition of reactive diluent

Immediately prior to curing, add the appropriate amount of diluent and 0.6 wt % DEAP (based on weight of polymer plus diluent). The weight percent of diluent is based on the total weight of prepolymer plus diluent. Mix for about 5 minutes to ensure a homogeneous solution.

iv) UV curing of cast films

Lay glass plate, 1 Mylar™ film and Teflon™ frame on top of one another in that order on level table. Pour appropriate amount of material (about 3 ml) in frame, being very careful to avoid bubble formation. Carefully place Mylar film on top of liquid/frame. Then place aluminum block on top of mylar film to smooth liquid.

The synthesis to the endtipped prepolymer can be carried out in one step as illustrated below:

where, for example, H2C=R'NCO isocyanatoethyl methacrylate (IEM).

The films were cured under a 20 watt mercury lamp for 30 minutes; each side faced the lamps for 15 minutes. The films were further annealed at 70° C. in a vacuum oven for 24 hours followed by storage in a desiccator. For PCL systems with low diluent content, the material crystallized during curing, therefore the films were placed on a hot plate during curing to prevent crystallization. Unless otherwise noted in the sample designations, all films were amorphous during curing.

An example sample designation is PCL-2000-IPDI-HEMA-NVP-20. The first 3 letters designate the soft segment (the polyol PCL) followed by the soft segment molecular weight, hard segment (the diisocyanate IPDI), the end-tipping vinyl group (HEMA), and finally reactive diluent type (NVP), and weight percent of reactive diluent. The weight percent of diluent is based on the total weight after adding reactive diluent.

Mechanical and viscosity measurements on PCL based systems were carried out to determine the effect of diluent concentration on solution viscosity of the uncured material and the tensile properties of the UV cured crosslinked material. The effect of the inclusion of an inhibitor, hyroquinone (HQ), on shelf life or pot life and photo-reaction rate was investigated as well.

Viscosity measurements were made of the prepolymer immediately prior to casting. Measurements were made on a Brookfield RVT viscometer equipped with a #21 small sample adapter. Calibration curves supplied by Brookfield were checked with viscosity standards. This adapter allowed for temperature control, which was accomplished through a recirculating water bath. All measurements were made at 50° C.

The viscosities of PCL-2000 based prepolymers for Examples 1, 2, 3, 4 and 8 are shown in Table 1. Measurements were made over a range of shear rates due to the wide range of viscosities. A least squares fit of a power law equation was used to extrapolate the viscosity to 1 $\sec^{-1}$. The power law exponent was essentially equal to unity in all cases indicating the uncured resins behaved as Newtonian fluids, viscosity a constant independent of shear rate, for the range of shear rates investigated. As the data in Table 1 show, diluent dramatically lowers the viscosity. A 20% increase in diluent concentration lowers the viscosity about an order of magnitude.

Uniaxial stress-strain measurements were made with a table model Instron machine at room temperature using a crosshead speed of 0.5 cm. Samples were cut from cured films using an ASTM D1708 die. All measurements represent the average of 3 tests. The engineering stress was calculated based on the initial area of the sample.

The ultimate strength, elongation and initial modulus of the UV-cured PCL based materials for Examples 1 to 8 are listed in Table 2. Up to approximately 50% diluent, the effect on elongation is slight. The elongation decreases at 60% and continues to decrease at 70% diluent. However, the ultimate breaking strength and the modulus continue to increase with increasing diluent content. The material becomes stiffer but more brittle-like at the highest concentrations.

A Rheometrics RSA II in the tension mode was used to acquire DMTA spectra. Samples were cut using an ASTM D1043 die with the ends cut to the proper length. The approximate test coupon dimensions are 23 mm×6.3 mm×1 mm thick. The autotension mode was used with a 120% force for pretension. Temperature steps of 3° C. were used with a 0.1 minute soak time. The frequency of the test was 16 Hz. The temperature range tested was −150° to 150° C.

The change in storage modulus E' showed the same trend as the initial tensile (Young's) modulus. The value increased as diluent content increased. The data for E' showed a fairly consistent glass transition at about −50° C.

The increase in modulus and strength with diluent content is probably due to an increase in cross link density. The addition of diluent could have allowed additional crosslinks to form through increased chain mobility due to the lowered viscosity or by actually increasing the crosslink functionality.

The effect of inhibitor on shelf life and reaction rate was studied. Hydroquinone (HQ) was used as the inhibitor. Shelf life of the material was tested by adding 0, 2000, and 5000 ppm of HQ to the PCL-2000-IPDI-HEMA-HEMA-20 of Example 2. The material was stored at 65° C. in a convection oven to accelerate the effect.

After 2 days, the material without any inhibitor showed a small amount of gel formation. The gel did not grow over a period of approximately one month. The other two materials have shown no evidence of gel formation over a month. The material that was used for the reaction rate study discussed below was stored at 45° C. for two weeks without any effect.

The effect of 500 ppm inhibitor on reaction rate was tested using Example 3, PCL-2000-IPDI-HEMA-HEMA-40. Material was cured under a 20 W mercury lamp at time intervals of 15 seconds up to the first minute and then at 1 minute intervals from 1 minute up to 5 minutes and the material was then dissolved in acetone. The amount of insoluble gel fraction was used to estimate reaction completeness. The effect was rather slight. HQ worked primarily as an inhibitor rather than a retarder. An inhibitor produces curves which have the same shape as the original curve, except these curves are shifted further in time. A retarder reduces the reaction rate. HQ may be a slight retarder as well.

EXAMPLES 9-18

Materials and Synthesis, Hydrolyzable Oligomers of Lactone Monomers

Copolymer of ε-Caprolactone/PDO at 50/50 by mole initial Composition (Oligomer for Examples 13 and 14)

A flame dried, 250 ml, round bottom single neck flask is charged with 57.07 g (0.50 mole of ε-caprolactone), 51.04 g (0.5 mole) p-dioxanone (PDO), 5.0 milliliters of distilled diethylene glycol, and 0.12 milliliters of stannous octoate (0.33 molar in toluene). The flask is fitted with a flame dried mechanical stirrer. The reactor is purged with nitrogen three times before venting with nitrogen. The reaction mixture is heated to 160° C. and maintained at this temperature for 24 hours, lowered to 110° C. and maintained there for 24 hours. The copolymer is dried for about 80 hours at 80° C. under high vacuum (0.1 mm Hg) to remove any unreacted monomer. The copolymer has an inherent viscosity (I.V.) of 0.18 dl/g in HFIP at 25° C. the mole ratio of PCL/Polydioxanone/PDO is found to be 52.7/45.7/1.6 by NMR (PCL and PDS refer to polymerized moieties of caprolactone and p-dioxanone, respectively).

Copolymer of ε-Caprolactone/PDO at 40/60 by mole initial Composition (Oligomer for Examples 11 and 12)

Procedure of Example 2 is substantially repeated, except that the reaction flask is charged with 45.66 g (0.4 mole) ε-caprolactone, 61.25 g (0.6 mole) of p-dioxanone, 4.75 ml of distilled diethylene glycol, and 0.12 ml of stannous octoate (0.33 molar in toluene). The copolymer has an I.V. of 0.17 dl/g in HFIP at 25° C. The mole ratio of PCL/Polydioxanone/PDO is found to be 57.3/40.0/2.7 by NMR.

Copolymer of ε-Caprolactone/L(−)Lactide at 60/40 by mole initial composition (Oligomer for Examples 9, 10, 17 and 18)

A flame dried, 250 ml, round bottom single neck flask is charged with 68.07 g (0.60 mole of ε-caprolactone), 57.65 g (0.4 mole) L(−) Lactide, 3.67 ml of propylene glycol (USP grade), and 0.10 ml of stannous octoate (0.33 molar in toluene). The flask is fitted with a flame dried mechanical stirrer. The reactor is purged with nitrogen three times before venting with nitrogen. The reaction mixture is heated to 160° C. and maintained at this temperature for 18-20 hours. The copolymer is dried for about 7 hours at 110° C. under high vacuum (0.1 mm Hg) to remove any unreacted monomer. The copolymer has an inherent viscosity (I.V.) of 0.16 dl/g in HFIP at 25° C. The mole ratio of PCL/PLA/caprolactone is found to be 48.8/50.0/1.2 by NMR (PCL and PLA refer to polymerized moieties of ε-caprolactone and L(−) lactide, respectively).

Copolymer of ε-Caprolactone/PDO at 80/20 by mole initial composition (Oligomer for Examples 15 and 16)

Procedure of Example 2 is substantially repeated, except that the reaction flask is charged with 182.62 g (1.6 mole) ε-caprolactone, 40.83 g (0.4 mole) of p-dioxanone, 10.0 ml of distilled diethylene glycol, and 0.242 ml of stannous octoate (0.33 molar in toluene). The copolymer has an I.V. of 0.19 dl/g in HFIP at 25° C. The mole ratio of PCL/Polydioxanone/PDO is found to be 71.3/26.8/1.9 by NMR.

Synthesis, Absorbable Urethane-Acrylates of the Invention

The procedure for the synthesis of the urethane acrylate and UV curing for Examples 9 to 18 was the same as that described above for the non-absorbable materials in Control Examples 1 to 8. The nominal weight average molecular of the each polyol is given in Table 3. A difunctional initiator, either diethylene glycol or propylene glycol was used in the synthesis of the polyol.

The sample designation for the absorbable examples is similar to that used for the non-absorbable controls. The soft segment polyol is designated, for example, as: PCL/PLA (60:40), a 60:40 mole ratio, random copolymer of caprolactone and lactide. The sample descriptions for Examples 8, 10, 12, 14, 16 and 18 are given in Table 3.

The methods of characterization of the prepolymers and cured polymers were the same as those used for the non-absorbable controls. In addition, to assess the bioabsorbability of the UV cured materials, weight loss in phosphate buffered solution (PBS), with a pH of 7.3 was measured. Approximately 0.1 grams of material was placed in 100 ml of PBS. Two temperatures were employed: 50° C. and 100° C. For the 50° C. study, the solution plus sample material was sealed in glass jars and placed in a convection oven. For the 100° C. study the solution was boiled at reflux. After the specified time period the samples were removed from the solution, dried in a vacuum oven at 70° C. for 48-hours and weighted. Different samples were used for each time period.

Two diisocyanates were evaluated. Substituting lysine triisocyanate (LTI), for IPDI resulted in a more brittle material. Reacting IPDI with a copolymer of type (caprolactone/absorbable monomer, PLA or PDO) did not noticeably affect the tensile properties of the UV cured film compared to the PCL based materials. Moreover, the rate of hydrolysis increased in proportion to the percentage of hydrolyzable comonomer in the polyol. Prepolymers with HEMA reactive diluent contents of 40% and 50% were synthesized and evaluated. These produced materials that would be suitable for stereolithographic applications, one of the uses of this invention. The prepolymers, listed in Table 3, were synthesized from the 4 absorbable oligomers (polyols). As shown in Table 3, the prepolymer viscosities as measured at 30° C. were similar to the PCL-2000 based materials.

After UV curing, samples were stamped into tensile specimens. Because of brittleness, some films could not be cut in this manner as noted in Table 4. Dynamic mechanical thermal analysis (DMTA) was carried out on materials stamped into a rectangular shape. Table 4 lists the results of tensile tests. Materials synthesized with LTI hard segments less ductile than those synthesized with IPDI. The LTI based material synthesized with a PCL/PDO copolymer did not show a noticeable soft segment glass transition (the usual transition at about −50° C.), in dynamic mechanical experiments, suggesting that phase separation was either not present or poor in this material. The PCL-2000-LTI-HEMA-HEMA-40 and 50 both showed a noticeable soft segment glass transition even though both materials were brittle. For IPDI based systems, replacing PCL-2000 with a copolymer of PCl and a bioabsorbable monomer changes the tensile properties very little. The comonomer causes a small increase in the modulus and the ultimate stress, with a small drop in ultimate elongation.

To evaluate the hydrolysis of the UV cured materials, weight loss in phosphate buffered solution (PBS) with a pH of 7.3 was measured at 50° C. and 100° C. Tables 5 and 6 contain the data for Examples 13 to 18 and the control Examples 3 and 4 for the hydrolysis tests. The maximum amount of weight loss at 50° C. was approximately 24% at 56 days and the maximum at 100° C. was about 40% at 72 hours. Weight loss was positively correlated to the level of hydrolyzable comonomer. The pure PCL material lost only a few percent of its weight. These results show that the rate of absorbability can be tailored easily by changing the amount and the type of bioabsorbable comonomer.

The feasibility of synthesizing bioabsorbable UV-curable urethane acrylates has been demonstrated. By replacing, for example, PCL oligomer with a ε-caprolactonebioabsorbable comonomer oligomer or other absorbable comonomer combinations the amount of hydrolysis can be controlled. For the ε-caprolactone based oligomers investigated, the synthesis of the urethane acrylate, the effects of reactive diluent, the rate of the photoreaction and the initial physical properties of the UV cured materials are similar to the non-absorbable PCL control. The addition of diluent increases the stiffness and decreases the viscosity with little effect on the ductility up to a certain concentration of diluent. Oligomer (polyol) molecular weight can be increased to improve the ductility. Oligomer molecular weight, type and end tipped group may be used to control ductility, while diluent content may be used to control viscosity and stiffness.

The results have shown the ability to synthesize bioabsorbable UV-curable prepolymers with physical properties which are adequate for use in many surgical applications. The viscosity of the prepolymer can be adjusted by using diluent so that materials can be utilized in a stereolithographic apparatus to produce useful surgical devices. Examples that come to mind are ligating clips and staples. However, it has been shown that by proper selection of diol, diisocyanate and reactive diluent, for example, that a range of tensile properties and rates of hydrolysis are possible. One skilled in the art of medical device design could envision a broad spectrum broad spectrum of devices that could be fabricated from these bioabsorbably UV-curable prepolymers.

TABLE 1

Viscosity of PCL-2000 based Prepolymers at 50° C. and 1 s⁻¹

| Example | Material | Viscosity (cp) |
|---|---|---|
| 1 | PCL-2000-IPDI-HEMA | 46,500 |
| 2 | PCL-2000-IPDI-HEMA-HEMA-20 | 2,430 |
| 3 | PCL-2000-IPDI-HEMA-HEMA-40 | 525 |
| 4 | PCL-2000-IPDI-HEMA-HEMA-50 | 230 |
| 8 | PCL-2000-LTI-HEMA-HEMA-50 | 750 |

*Measured at 30° C.

TABLE 2

Tensile Properties of PCL-2000 Based Cured Materials

| Example | Material | Modulus | Ultimate Elongation | Ultimate Stress |
|---|---|---|---|---|
| 1 | PCL-2000-IPDI-HEMA | 900 | 125 | 1860 |
| 2 | PCL-2000-IPDI-HEMA-HEMA-20 | 10900 | 150 | 2350 |
| 3 | PCL-2000-IPDI-HEMA-HEMA-40 | 63500 | 125 | 3655 |
| 4 | PCL-2000-IPDI-HEMA-HEMA-50 | 47000 | 115 | 3205 |
| 5 | PCL-2000-IPDI-HEMA-HEMA-60 | 77900 | 85 | 4395 |
| 6 | PCL-2000-IPDI-HEMA-HEMA-70 | 100100 | 52 | 4395 |
| 7 | PCL-2000-LTI-HEMA-HEMA-40 | 87000 | 39 | 2950 |
| 8 | PCL-2000-LTI-HEMA-HEMA-50 | n/a# | 29 | n/a# |

The values for this sample were lost due to a problem with the data acquisition system for the tensile tester.

TABLE 3

Viscosity at 30° C. and 1 s⁻¹ of Hydrolyzable Oligomer-Based Prepolymers for Example 10, 12, 14, 16 and 18

| Example | material | Molecular Weight of Diol | Prepolymer Viscosity (centipoise) |
|---|---|---|---|
| 10 | PCL/PLA(60:40)-LTI-HEMA-HEMA-50 | 2230 | 240 |
| 12 | PCL/PDO(40:60)-LTI-HEMA-HEMA-50 | 1580 | 385 |
| 14 | PCL/PDO(50:50)-IPDI-HEMA-HEMA-50 | 1664 | 355 |
| 16 | PCL/PDO(80:20)-IPDI-HEMA-HEMA-50 | 1919 | 295 |
| 18 | PCL/PLA(60:40)-IPDI-HEMA-HEMA-50 | 2230 | 560 |

TABLE 4

Tensile Test Results of Hydrolyzable Oligomer-Based Cured Materials For Examples 9 to 18

| Example | Material | Ultimate Elongation | Ultimate Stress psi | Modulus psi |
|---|---|---|---|---|
| 9 | PCL/PLA(60:40)-LTI-HEMA-HEMA-40 | * | * | * |
| 10 | PCL/PLA(60:40)-LTI-HEMA-HEMA-50 | * | * | * |
| 11 | PCL/PDO(40:60)-LTI-HEMA-HEMA-40 | 30 | 4350 | 132000 |
| 12 | PCL/PDO(40:60)-LTI-HEMA-HEMA-50 | 16 | 4600 | 117000 |
| 13 | PCL/PDO(50:50)-IPDI-HEMA-HEMA-40 | 85 | 4010 | 91500 |
| 14 | PCL/PDO(50:50)-IPDI-HEMA-HEMA-50 | 72 | 4400 | 95700 |
| 15 | PCL/PDO(80:20)-IPDI-HEMA-HEMA-40 | 75 | 2800 | 70850 |
| 16 | PCL/PDO(80:20)-IPDI-HEMA-HEMA-50 | 75 | 3950 | 109500 |
| 17 | PCL/PLA(60:40)-IPDI-HEMA-HEMA-40 | 100 | 4900 | 103700 |
| 18 | PCL/PLA(60:40)-IPDI-HEMA-HEMA-50 | 108 | 5350 | 115000 |

*The sample was too brittle to test

TABLE 5

Weight Loss (%) in PBS at 50° C. of Hydrolyzable Oligomer-Based Cured Materials For Examples 13 to 18 and Control Examples 3 and 4

| Example | Material | 1 Day | 7 Days | 14 Days | 28 Days | 56 Days |
|---|---|---|---|---|---|---|
| 13 | PCL/PDO(50:50)-IPDI-HEMA-HEMA-40 | 1.4 | 2.2 | 5.6 | 17.7 | 22.0 |
| 14 | PCL/PDO(50:50)-IPDI-HEMA-HEMA-50 | 1.8 | 2.7 | 8.5 | 16.2 | n/a* |
| 15 | PCL/PDO(80:20)-IPDI-HEMA-HEMA-40 | 0.9 | 1.5 | 2.9 | 6.6 | 9.0 |
| 16 | PCL/PDO(80:20)-IPDI-HEMA-HEMA-50 | 1.1 | 2.0 | 3.3 | 7.7 | 8.3 |
| 17 | PCL/PLA(60:40)-IPDI-HEMA-HEMA-40 | 0.8 | 2.4 | 6.2 | 14.5 | 19.4 |
| 18 | PCL/PLA(60:40)-IPDI-HEMA-HEMA-50 | 1.0 | 1.9 | 5.8 | 13.9 | 23.7 |
| 3 | PCL-2000-IPDI-HEMA-HEMA-40 | 0.5 | 0.3 | 0.3 | 0.5 | 0.5 |
| 4 | PCL-2000-IPDI-HEMA-HEMA-50 | 1.5 | 1.7 | 1.4 | 1.6 | 3.1 |

*n/a: not available (data was not collected for these samples for this time period)

TABLE 6

Weight Loss (%) in PBS at 100° C. of Hydrolyzable Oligomer-Based cured Materials For Examples 13 to 18 and Control Examples 3 and 4

| Example | Material | 2 Hours | 8 Hours | 24 Hours | 72 Hours |
|---|---|---|---|---|---|
| 13 | PCL/PDO(50:50)-IPDI-HEMA-HEMA-40 | 2.0 | 8.9 | 28.5 | 24.6 |
| 14 | PCL/PDO(50:50)-IPDI-HEMA-HEMA-50 | 1.6 | 8.7 | 23.9 | 29.5 |
| 15 | PCL/PDO(80:20)-IPDI-HEMA-HEMA-40 | 2.2 | 6.5 | 18.3 | 35.0 |
| 16 | PCL/PDO(80:20)-IPDI-HEMA-HEMA-50 | 0.6 | 5.0 | 12.9 | 30.5 |
| 17 | PCL/PLA(60:40)-IPDI-HEMA-HEMA-40 | 0.9 | 10.3 | 28.9 | 41.2 |
| 18 | PCL/PLA(60:40)-IPDI-HEMA-HEMA-50 | 1.4 | 12.5 | 29.4 | 37.4 |
| 3 | PCL-2000-IPDI-HEMA-HEMA-40 | n/a | 3.5 | 4.7 | +0.5 |
| 4 | PCL-2000-IPDI-HEMA-HEMA-50 | n/a | 4.5 | 11.9 | n/a | n/a: not available

We claim:

1. A shaped bioabsorbable medical device made by stereolithography from a crosslinked, urethane-acrylate prepolymer comprising the reaction product of the following:
   a) a urethane prepolymer of a polyfunctional isocyanate and a hydrolyzable oligomer of an anhydrous cyclic ester of a hydroxy acid, and
   b) an end tipping amount of an acrylate selected from the group consisting of hydroxy acrylate and hydroxy methacrylate.

2. The bioabsorbable medical device of claim 1 wherein the anhydrous cyclic ester of a hydroxy acid is selected from the group consisting of lactide, glycolide, paradioxanone, trimethylene carbonate and a mixture of two or more thereof.

3. The bioabsorbable medical device of claim 1 wherein the anhydrous cyclic ester of a hydroxy acid is a mixture of ε-caprolactone and a second anhydrous cyclic ester of a hydroxy acid selected from the group consisting of lactide, glycolide, para-dioxanone and trimethylene carbonate.

4. The absorbable medical device of claim 3 wherein the anhydrous cyclic ester of a hydroxy acid is a mixture of ε-caprolactone and the second anhydrous cyclic ester of a hydroxy acid is selected from the group consisting of para-dioxanone and lactide.

5. The bioabsorbable medical device of claim 4 wherein the mole ratio of ε-caprolactone to the second anhydrous cyclic ester of a hydroxy acid is between about 10:90 to about 90:10.

6. The bioabsorbable medical device of claim 5 wherein the mole ratio of ε-caprolactone to the second anhydrous cyclic ester of a hydroxy acid is between about 20:80 to about 80:20.

7. The bioabsorbable medical device of claim 6 wherein the mole ratio of ε-caprolactone to paradioxanone or lactide is between about 60:40 to about 40:60.

8. The bioabsorbable medical device of claim 7 wherein the weight average molecular weight of the hydrolyzable oligomer is between about 500 to 5000.

9. The bioabsorbable medical device of claim 8 wherein the weight average molecular weight of the hydrolyzable oligomer is between about 2000 to about 3000.

10. The bioabsorbable medical device of claim 9 wherein the polyfunctional isocyanate is toluene diisocyanate, isophorone diisocyanate, (meta) tetramethyl xylene diisucyanate, 4, 4'methylene diphenylene diisocyanate, lysine triisocyanate, or isocyanatoethyl methacrylate.

11. The bioabsorbable medical device of claim 10 wherein the polyfunctional isocyanate is toluene diisocyanate or isophorone diisocyanate.

12. The bioabsorbable medical device of claim 11 wherein the acrylate is selected from the group consisting of hydroxyethyl methacrylate and hydroxyethyl acrylate.

13. The bioabsorbable medical device of claim 12 wherein the acrylate is hydroxyethyl methacrylate.

14. The bioabsorbable medical device of claim 13 wherein the endtipping amount of hydroxyethyl methacrylate is defined by a mole ratio of the urethane prepolymer to hydroxyethyl methacrylate of between about 2:1 to about 1:2.

15. The bioabsorbable medical device of claim 14 wherein the endtipping amount of hydroxyethyl methacrylate is defined by a mole ratio of the urethane prepolymer to hydroxyethyl methacrylate of about 1:1.

16. The bioabsorbable medical device of claim 15 wherein the urethane-acrylate prepolymer is crosslinked in the presence of a reactive diluent.

17. The bioabsorbable medical device of claim 16 wherein the amount of reactive diluent is between about 20 to 70 weight percent of the urethane-acrylate prepolymer reaction mixture.

18. The bioabsorbable medical device of claim 17 wherein the amount of reactive diluent is between about 40 to 50 weight percent of the urethane-acrylate prepolymer reaction mixture.

19. The bioabsorbable medical device of claim 18 wherein the reactive diluent is selected from the group consisting of N-vinyl pyrrolidone and hydroxyethyl methacrylate.

20. The bioabsorbable medical device of claim 1 wherein the medical device is a surgical staple or clip.

* * * * *